(12) United States Patent
Lamoureux et al.

(10) Patent No.: US 7,988,611 B2
(45) Date of Patent: Aug. 2, 2011

(54) AFTER-LOADER FOR POSITIONING IMPLANTS FOR NEEDLE DELIVERY IN BRACHYTHERAPY AND OTHER RADIATION THERAPY

(75) Inventors: Gary A. Lamoureux, Woodbury, CT (US); Warren W. Johnston, Thomaston, CT (US)

(73) Assignee: Biocompatibles UK Limited, Farnham, Surrey (GB)

( * ) Notice: Subject to any disclaimer, the term of this patent is extended or adjusted under 35 U.S.C. 154(b) by 1307 days.

(21) Appl. No.: 11/592,909

(22) Filed: Nov. 3, 2006

(65) Prior Publication Data

US 2007/0265488 A1 Nov. 15, 2007

Related U.S. Application Data

(60) Provisional application No. 60/799,161, filed on May 9, 2006, provisional application No. 60/847,834, filed on Sep. 28, 2006.

(51) Int. Cl.
*A61M 36/00* (2006.01)
(52) U.S. Cl. .......................................................... 600/7
(58) Field of Classification Search ................ 600/1–8
See application file for complete search history.

(56) References Cited

U.S. PATENT DOCUMENTS

| | | |
|---|---|---|
| 1,578,945 A | 3/1926 | Withers |
| 2,067,589 A | 1/1937 | Antrim |
| 2,153,889 A | 4/1939 | Frederick |
| 2,575,138 A | 11/1951 | Slaughter |
| 2,668,162 A | 2/1954 | Lowe |
| 2,703,316 A | 3/1955 | Schneider |
| 2,758,987 A | 8/1956 | Salzberg |
| 3,187,752 A | 6/1965 | Glick |
| 3,297,033 A | 1/1967 | Schmitt et al. |
| 3,351,049 A | 11/1967 | Lawrence |
| 3,565,869 A | 2/1971 | De Prospero |
| 3,636,956 A | 1/1972 | Schneider |
| 3,752,630 A | 8/1973 | Takagi |
| 3,811,426 A | 5/1974 | Culver et al. |
| 3,839,297 A | 10/1974 | Wasserman et al. |
| 3,936,414 A | 2/1976 | Wright et al. |
| 4,052,988 A | 10/1977 | Doddi |

(Continued)

FOREIGN PATENT DOCUMENTS

EP 0 030 822 B1 9/1983
(Continued)

OTHER PUBLICATIONS

International Search Report, in connection with Application No. PCT/US2007/68595 dated Feb. 13, 2008, 5 pages.
(Continued)

*Primary Examiner* — Samuel Gilbert
(74) *Attorney, Agent, or Firm* — Fliesler Meyer LLP

(57) ABSTRACT

In one embodiment an after-loader for providing an implant to a hollow needle, the after-loader comprising a body having a distal end including a bevel for receiving a hub of a seed lock needle, and a bore therethrough for receiving a hub of a MICK® needle; a proximal end having a funnel shaped opening; a shield adapted to be provided over the body; and wherein the distal end further includes a taper along a portion of a distance from the distal end to the proximal end for providing a friction fit to a shield. This abstract is not intended to be a complete description of the invention.

12 Claims, 10 Drawing Sheets

U.S. PATENT DOCUMENTS

| | | |
|---|---|---|
| 4,086,914 A | 5/1978 | Moore |
| 4,141,087 A | 2/1979 | Shalaby et al. |
| 4,167,179 A | 9/1979 | Kirsch |
| 4,402,308 A | 9/1983 | Scott |
| 4,416,308 A | 11/1983 | Bower |
| 4,416,659 A | 11/1983 | Simpson et al. |
| 4,441,496 A | 4/1984 | Shalaby et al. |
| 4,452,973 A | 6/1984 | Casey et al. |
| 4,473,670 A | 9/1984 | Kessidis |
| 4,509,506 A | 4/1985 | Windorski et al. |
| 4,510,295 A | 4/1985 | Bezwada |
| 4,612,923 A | 9/1986 | Kronenthal |
| 4,638,809 A * | 1/1987 | Kuperus .................. 600/4 |
| 4,646,741 A | 3/1987 | Smith |
| 4,689,424 A | 8/1987 | Shalaby et al. |
| 4,697,575 A | 10/1987 | Horowitz |
| 4,702,228 A | 10/1987 | Russell et al. |
| 4,741,337 A | 5/1988 | Smith |
| 4,754,745 A | 7/1988 | Horowitz |
| 4,772,287 A | 9/1988 | Ray et al. |
| 4,784,116 A | 11/1988 | Russell, Jr., et al. |
| 4,815,449 A | 3/1989 | Horowitz |
| 4,847,505 A | 7/1989 | Suthanthiran |
| 4,891,165 A | 1/1990 | Suthanthiran |
| 4,916,209 A | 4/1990 | Fung et al. |
| 4,936,823 A | 6/1990 | Colvin et al. |
| 4,946,435 A | 8/1990 | Suthanthiran et al. |
| 5,022,940 A | 6/1991 | Mehoudar |
| 5,242,373 A * | 9/1993 | Scott et al. ............... 600/7 |
| 5,264,540 A | 11/1993 | Cooper et al. |
| 5,339,812 A | 8/1994 | Hardy et al. |
| 5,391,139 A | 2/1995 | Edmundson |
| 5,397,816 A | 3/1995 | Reilley et al. |
| 5,403,576 A | 4/1995 | Lin et al. |
| 5,405,309 A | 4/1995 | Carden, Jr. |
| 5,460,592 A | 10/1995 | Langton et al. |
| 5,521,280 A | 5/1996 | Reilly et al. |
| 5,713,828 A | 2/1998 | Coniglione |
| 5,755,704 A | 5/1998 | Lunn |
| 5,761,877 A | 6/1998 | Quandt |
| 5,833,593 A | 11/1998 | Liprie |
| 5,860,909 A | 1/1999 | Mick et al. |
| 5,928,130 A | 7/1999 | Schmidt |
| 5,938,583 A | 8/1999 | Grimm |
| 6,007,475 A | 12/1999 | Slater et al. |
| 6,010,446 A | 1/2000 | Grimm |
| 6,039,684 A | 3/2000 | Ildstad et al. |
| 6,053,858 A | 4/2000 | Bueche et al. |
| 6,080,099 A | 6/2000 | Slater et al. |
| 6,086,942 A | 7/2000 | Carden et al. |
| 6,099,457 A | 8/2000 | Good |
| 6,132,359 A | 10/2000 | Bolenbaugh |
| 6,132,677 A | 10/2000 | Ohriner |
| 6,132,947 A | 10/2000 | Honan et al. |
| 6,159,143 A | 12/2000 | Lennox |
| 6,163,947 A | 12/2000 | Coniglione |
| 6,200,255 B1 | 3/2001 | Yu |
| 6,200,256 B1 | 3/2001 | Weinberger |
| 6,200,258 B1 | 3/2001 | Slater et al. |
| 6,213,932 B1 | 4/2001 | Schmidt |
| 6,248,057 B1 | 6/2001 | Mavity et al. |
| 6,264,599 B1 | 7/2001 | Slater et al. |
| 6,264,600 B1 | 7/2001 | Grimm |
| 6,273,851 B1 | 8/2001 | Slater et al. |
| 6,283,911 B1 | 9/2001 | Keren |
| 6,312,374 B1 | 11/2001 | von Hoffmann |
| 6,319,190 B1 | 11/2001 | Schmidt et al. |
| 6,327,490 B1 | 12/2001 | Spetz |
| 6,358,195 B1 * | 3/2002 | Green et al. ............. 600/7 |
| 6,360,116 B1 | 3/2002 | Jackson, Jr. et al. |
| 6,387,034 B1 | 5/2002 | Lee |
| 6,398,709 B1 | 6/2002 | Ehr et al. |
| 6,403,916 B1 | 6/2002 | Spooner et al. |
| 6,419,621 B1 | 7/2002 | Sioshansi et al. |
| 6,428,504 B1 | 8/2002 | Riaziat et al. |
| 6,436,026 B1 | 8/2002 | Sioshansi et al. |
| 6,438,401 B1 | 8/2002 | Cheng et al. |
| 6,450,937 B1 | 9/2002 | Mercereau et al. |
| 6,450,938 B1 | 9/2002 | Miller |
| 6,450,939 B1 | 9/2002 | Grimm |
| 6,471,631 B1 | 10/2002 | Slater et al. |
| 6,472,675 B2 | 10/2002 | White et al. |
| 6,474,535 B1 | 11/2002 | Shanks et al. |
| 6,482,178 B1 | 11/2002 | Andrews et al. |
| 6,497,646 B1 | 12/2002 | Candelaria et al. |
| 6,500,109 B2 | 12/2002 | Tokita et al. |
| 6,514,193 B2 | 2/2003 | Kaplan |
| 6,537,192 B1 | 3/2003 | Elliott et al. |
| 6,537,193 B1 | 3/2003 | Lennox |
| 6,539,247 B2 | 3/2003 | Spetz |
| 6,549,802 B2 | 4/2003 | Thornton |
| 6,554,760 B2 | 4/2003 | Lamoureux et al. |
| 6,561,967 B2 | 5/2003 | Schmidt |
| 6,569,076 B1 | 5/2003 | Larsen et al. |
| 6,572,525 B1 | 6/2003 | Yoshizumi |
| 6,572,527 B2 | 6/2003 | Steele, Sr. et al. |
| 6,575,888 B2 | 6/2003 | Zamora et al. |
| 6,585,633 B2 | 7/2003 | Vitali et al. |
| 6,595,908 B2 | 7/2003 | Loffler et al. |
| 6,599,231 B1 | 7/2003 | Elliott et al. |
| 6,612,976 B2 | 9/2003 | Rosenthal et al. |
| 6,616,593 B1 | 9/2003 | Elliott et al. |
| 6,616,594 B2 | 9/2003 | Fontayne et al. |
| 6,626,817 B2 | 9/2003 | Luth |
| 6,632,176 B2 | 10/2003 | McIntire et al. |
| 6,638,205 B1 | 10/2003 | Chan et al. |
| 6,638,206 B2 | 10/2003 | Green et al. |
| 6,639,237 B2 | 10/2003 | Pedersen et al. |
| 6,648,811 B2 | 11/2003 | Sierocuk et al. |
| 6,656,106 B2 | 12/2003 | Schmidt |
| 6,656,107 B1 | 12/2003 | Pedersen et al. |
| 6,669,621 B2 | 12/2003 | O'Hara et al. |
| 6,669,622 B2 | 12/2003 | Reed et al. |
| 6,679,824 B1 | 1/2004 | Reed et al. |
| 6,682,471 B2 | 1/2004 | Stelle et al. |
| 6,689,043 B1 | 2/2004 | McIntire et al. |
| 6,709,381 B2 | 3/2004 | Munro, III |
| 6,716,156 B2 | 4/2004 | Menuhr et al. |
| 6,723,037 B2 | 4/2004 | Hamazaki et al. |
| 6,723,052 B2 | 4/2004 | Mills |
| 6,726,617 B1 * | 4/2004 | Schmidt ..................... 600/7 |
| 6,746,661 B2 | 6/2004 | Kaplan |
| 6,749,554 B1 | 6/2004 | Snow et al. |
| 6,752,753 B1 | 6/2004 | Hoskins et al. |
| 6,755,775 B2 | 6/2004 | Kalas et al. |
| 6,761,680 B2 | 7/2004 | Terwilliger et al. |
| 6,786,858 B2 | 9/2004 | Terwilliger et al. |
| 6,790,170 B2 | 9/2004 | Moody et al. |
| 6,800,055 B2 | 10/2004 | Amols et al. |
| 6,805,898 B1 | 10/2004 | Wu et al. |
| 6,820,318 B2 | 11/2004 | Terwilliger et al. |
| 6,837,844 B1 | 1/2005 | Ellard et al. |
| 6,846,283 B2 | 1/2005 | Green et al. |
| 6,905,455 B2 | 6/2005 | Rapach et al. |
| 6,911,000 B2 | 6/2005 | Mick et al. |
| 6,926,657 B1 | 8/2005 | Reed et al. |
| 6,969,344 B2 | 11/2005 | Drobnik et al. |
| 6,989,543 B2 | 1/2006 | Drobnik et al. |
| 7,008,367 B2 | 3/2006 | Visscher et al. |
| 7,060,020 B2 | 6/2006 | Terwilliger et al. |
| 7,074,291 B2 | 7/2006 | Terwilliger et al. |
| 7,083,566 B2 | 8/2006 | Tornes et al. |
| 7,094,198 B2 | 8/2006 | Terwilliger et al. |
| 7,118,523 B2 | 10/2006 | Loffler et al. |
| 7,211,039 B2 | 5/2007 | Lamoureux et al. |
| 7,267,643 B2 | 9/2007 | Koster et al. |
| 7,322,928 B2 | 1/2008 | Reed et al. |
| 7,497,818 B2 | 3/2009 | Terwilliger et al. |
| 7,601,113 B2 | 10/2009 | Lebovic et al. |
| 7,887,476 B2 * | 2/2011 | Hermann et al. ............. 600/3 |
| 2001/0008951 A1 | 7/2001 | Sierocuk et al. |
| 2001/0047185 A1 | 11/2001 | Satz |
| 2002/0066824 A1 | 6/2002 | Floyd et al. |
| 2002/0077522 A1 | 6/2002 | Hamazaki et al. |
| 2003/0084988 A1 | 5/2003 | Terwilliger et al. |
| 2003/0092958 A1 | 5/2003 | Terwilliger et al. |
| 2003/0181794 A1 | 9/2003 | Rini et al. |

| | | | |
|---|---|---|---|
| 2003/0191355 | A1 | 10/2003 | Ferguson |
| 2004/0024453 | A1 | 2/2004 | Castillejos |
| 2004/0034312 | A1 | 2/2004 | Koster et al. |
| 2004/0109823 | A1 | 6/2004 | Kaplan |
| 2004/0158117 | A1 | 8/2004 | Drobnik et al. |
| 2004/0158118 | A1 | 8/2004 | Drobnik et al. |
| 2004/0225174 | A1 | 11/2004 | Fuller et al. |
| 2005/0049490 | A1 | 3/2005 | Mills |
| 2005/0261541 | A1 | 11/2005 | Henderson et al. |
| 2006/0052654 | A1 | 3/2006 | Drobnik et al. |
| 2006/0063960 | A1 | 3/2006 | Wissman et al. |
| 2006/0094983 | A1 | 5/2006 | Burbank et al. |
| 2006/0121080 | A1 | 6/2006 | Lye et al. |
| 2006/0177379 | A1 | 8/2006 | Asgari |
| 2007/0224234 | A1 | 9/2007 | Steckel et al. |
| 2007/0238983 | A1 | 10/2007 | Suthanthiran |
| 2008/0004483 | A1* | 1/2008 | Tarone et al. .......... 600/8 |

FOREIGN PATENT DOCUMENTS

| | | |
|---|---|---|
| EP | 0 292 630 A | 11/1988 |
| EP | 0 466 681 B1 | 1/1992 |
| EP | 0 668 088 A | 8/1995 |
| EP | 0993 843 A | 4/2000 |
| EP | 1 240 920 A | 9/2002 |
| WO | WO 00/64538 | 2/2000 |
| WO | WO 00/61229 | 10/2000 |
| WO | WO 2008/106586 | 9/2008 |

OTHER PUBLICATIONS

Merrick et al., "Seed Fixity in the Prostate/Periprostatic Region Following Brachytherapy," IJROBP vol. 46(1):pp. 215-220 (2000).

Poggi et al., "Marker Seed Migration in Prostate Localization," IJROBP vol. 56(5):pp. 1248-1251 (2003).

Tapen et al., "Reduction of Radioactive Seed Embolization to the Lung Following Prostate Brachtherapy," IJROBP vol. 42(5):pp. 1063-1067 (1998).

Meiller, R., "Advances May Improve Prostate Cancer Treatment," Board of Regents of the University of Wisconsin System, http://www.news.wisc.edu/11899.html, 3 pages (Dec. 1, 2005).

Alvaro Martinez, et al; "Sterilization of $^{125}$I Seeds Encased in Vicryl Sutures for Permanent Interstitial Implantation"; Intl. J. Radiation Oncology Biol. Phys. vol. 5, pp. 411-413; Pergamen Press Ltd., 1979.

Van't Riet, "Ultrasonically Guided Transperineal Seed Implantation of the Prostate: Modification of the Technique and Qualitative Assessment of Implants", Intl. J. Rad. Onc. Biol. Phys. 24(3): 555-558 (1992).

Middleton et al., "Synthetic Biodegradable Polymers as Medical Devices", Med. Plas. Biomat. (Mar. 1998).

http://investor.mentorcopr.com/news/20010122-32414.cfm, "Mentor Acquires Breakthrough Brachytherapy Technology" (Jan. 25, 2002).

Webster's II New Riverside University Dictionary, p. 191, 1984.

Medi-Physics brochure entitled I-125 Seeds. No. 6711, Medi-Physics, Inc. Arlington Heights Il. 60004, USA; Revised. Oct. 1999, 2 pages.

Medi-Physics brochure entitled I-125 Seeds. No. 7000; Medi-Physics, Inc. Arlington Heights Il. 60004, USA; Revised. Oct. 1999, 2 pages.

Amersham Health; "EchoSeed™"; http://www.amershamhealth-us.com/echoseed/ printed Nov. 19, 2003.

Amersham Health; "Rapid Strand Indications"; Http;//www.amershamhealth-us.com/products/index.htp?a=i&i=38; printed Nov. 19, 2003.

Amersham Health; "OncoSeed Indications"; http://www.amershamhealth-us.com/oncoseed/; printed Nov. 19, 2003.

RadioMed: Innovative Products for Radiation, "The Visicoil Advantage . . . for Image Guided Radiation Therapy," http://www.radiomed.com/visicoil/, at lease as early as Aug. 2003.

Oncura, "RapidStrandR$_x$: The Logical Choice for Improved Dosimetry," Ocura Inc., Plymouth Meeting, PA, Apr. 2005.

* cited by examiner

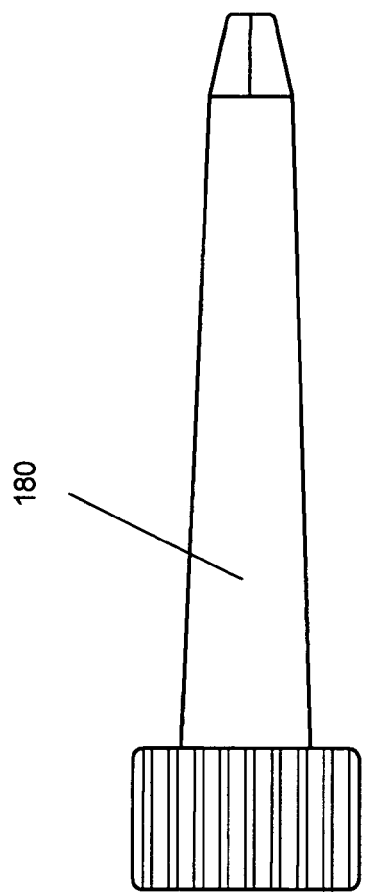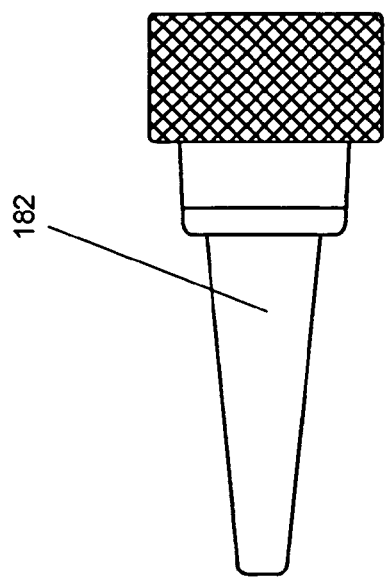
FIG. 4A
FIG. 4B

AFTER-LOADER FOR POSITIONING IMPLANTS FOR NEEDLE DELIVERY IN BRACHYTHERAPY AND OTHER RADIATION THERAPY

CLAIM OF PRIORITY

This application claims priority to the following U.S. Provisional Applications, which are incorporated herein by reference.

U.S. Provisional Application Ser. No. 60/799,161, entitled "After-loader for Positioning Implants for Needle Delivery in Brachytherapy and Other Radiation Therapy," by Gary Lamoureux et al., filed May 9, 2006;

U.S. Provisional Application Ser. No. 60/847,834, by Gary Lamoureux et al., entitled "After-loader for Positioning Implants for Needle Delivery in Brachytherapy and Other Radiation Therapy," filed Sep. 28, 2006.

FIELD OF THE INVENTION

This invention relates to radiotherapy. More particularly, it relates to applicators for positioning implants e.g., for use in brachytherapy.

BACKGROUND

Brachytherapy is a general term covering medical treatment which involves placement of radioactive sources near a diseased tissue and can involve the temporary or permanent implantation or insertion of radioactive sources into the body of a patient. The radioactive sources are located in proximity to the area of the body which is being treated. A high dose of radiation can thereby be delivered to the treatment site with relatively low doses of radiation to surrounding or intervening healthy tissue. Exemplary radioactive sources include radioactive seeds, radioactive rods and radioactive coils.

Brachytherapy has been used or proposed for use in the treatment of a variety of conditions, including arthritis and cancer. Exemplary cancers that can be treated using brachytherapy include breast, brain, liver and ovarian cancer and especially prostate cancer in men. For a specific example, treatment for prostate cancer can involve the temporary implantation of radioactive sources (e.g., rods) for a calculated period, followed by the subsequent removal of the radioactive sources. Alternatively, radioactive sources (e.g., seeds) can be permanently implanted in the patient and left to decay to an inert state over a predictable time. The use of temporary or permanent implantation depends on the isotope selected and the duration and intensity of treatment required.

Permanent implants for prostate treatment include radioisotopes with relatively short half lives and lower energies relative to temporary seeds. Exemplary permanently implantable sources include iodine-125, palladium-103 or cesium-131 as the radioisotope. The radioisotope can be encapsulated in a biocompatible casing (e.g., a titanium casing) to form a "seed" which is then implanted. Temporary implants for the treatment of prostate cancer may involve iridium-192 as the radioisotope. For temporary implants, radioactive rods are often used.

Conventional radioactive seeds are typically smooth sealed containers or capsules of a biocompatible material, e.g., titanium or stainless steel, containing a radioisotope within the sealed chamber that permits radiation to exit through the container/chamber walls. Other types of implantable radioactive sources for use in radiotherapy are radioactive rods and radioactive coils, as mentioned above.

Preferably, the implantation of radioactive sources for brachytherapy is carried out using minimally-invasive techniques such as, e.g., techniques involving needles and/or catheters. It is possible to calculate a desired location for each radioactive source which will give the desired radiation dose profile. This can be done using knowledge of the radioisotope content of each source, the dimensions of the source, accurate knowledge of the dimensions of the tissue or tissues in relation to which the source is to be placed, plus knowledge of the position of the tissue relative to a reference point. The dimensions of tissues and organs within the body for use in such dosage calculations can be obtained prior to or during placement of the radioactive sources by using conventional diagnostic imaging techniques including X-ray imaging, magnetic resonance imaging (MRI), computed tomography (CT) imaging, fluoroscopy and ultrasound imaging.

During the placement of the radioactive sources into position, a surgeon can monitor the position of tissues such as the prostate gland using, e.g., ultrasound imaging or fluoroscopy techniques which offer the advantage of low risk and convenience to both patient and surgeon. The surgeon can also monitor the position of the relatively large needle used in implantation procedures using ultrasound or other imaging.

BRIEF DESCRIPTION OF THE DRAWINGS

FIG. 4A is an embodiment of a distal end plug for use with the after-loader of FIG. 2; FIG. 4B is an embodiment of a proximal end plug for use with the after-loader of FIG. 2.

DETAILED DESCRIPTION

Brachytherapy typically employs a hollow needle that is insertable through a template and into a patient's body. A typical template used to guide and/or inform the positioning of hollow needles at the surgical site can provide access to more than one hundred locations. The number of locations can be so numerous that a typical pitch between needle access points can include a pitch of 5 mm.

One or more implants are provided to the hollow needle for delivery at a surgical site. A distal end of the hollow needle is typically inserted to the desired depth, thus at least one of the implant is typically urged to approximately the proximal end of the hollow needle. The implants can include a radioactive source. The radioactive source can be a radioactive seed, a radioactive rod, or a radioactive coil, but is not limited thereto. The radioactive source can further be an anchor seed, which is a seed having an outer shape and/or outer coating adapted to resist movement once implanted at a desired location within the patient, for example, as disclosed in U.S. patent application Ser. No. 11/187,411, entitled "Implants for Use in Brachtherapy and Other Radiation Therapy That Resist Migration and Rotation," filed Jul. 22, 2005, which is incorporated herein by reference. Alternatively, the implant can be some other object and need not be radioactive, e.g. the implant can be a spacer, or a marker. For reasons of convenience, embodiments will be described with reference to a "seed," however it will be understood that embodiments can additionally or alternatively be used with any implant.

Figure 1:
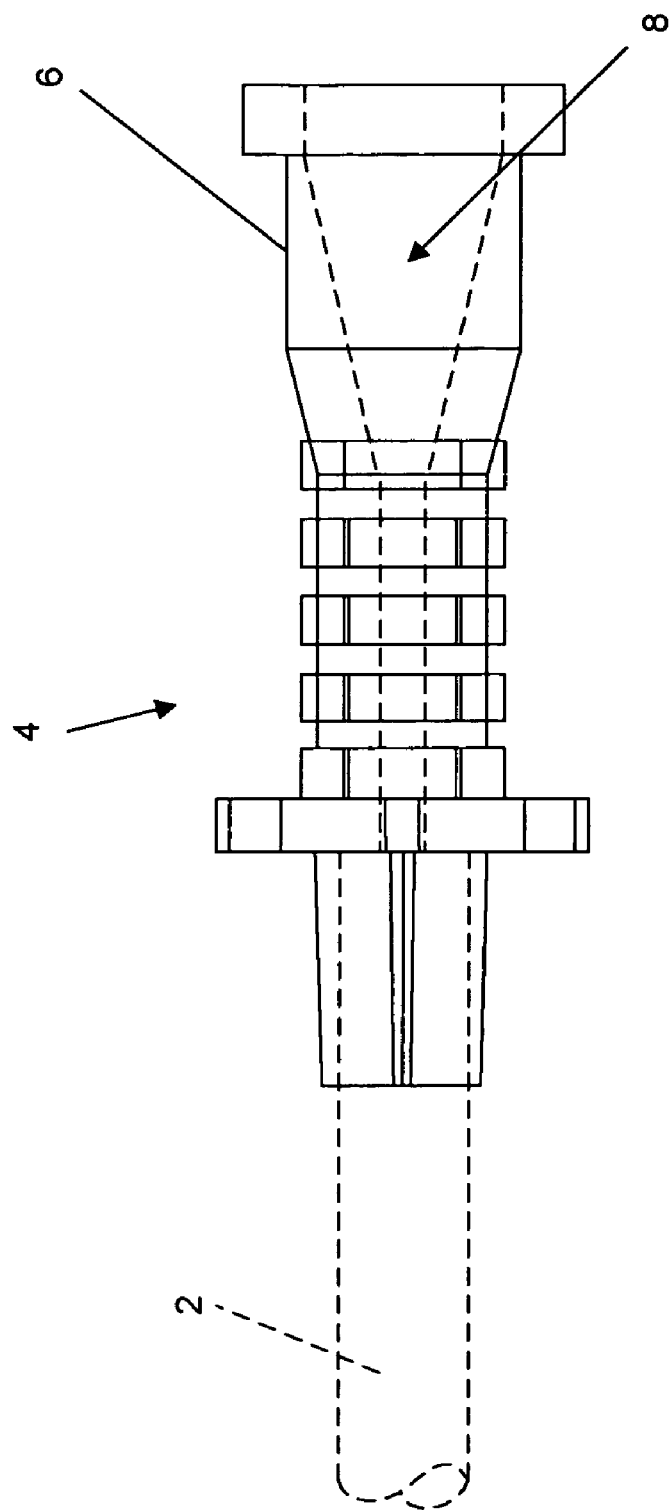
FIG. 1 is a side view of a hub of a seed lock needle.
Figure 2:
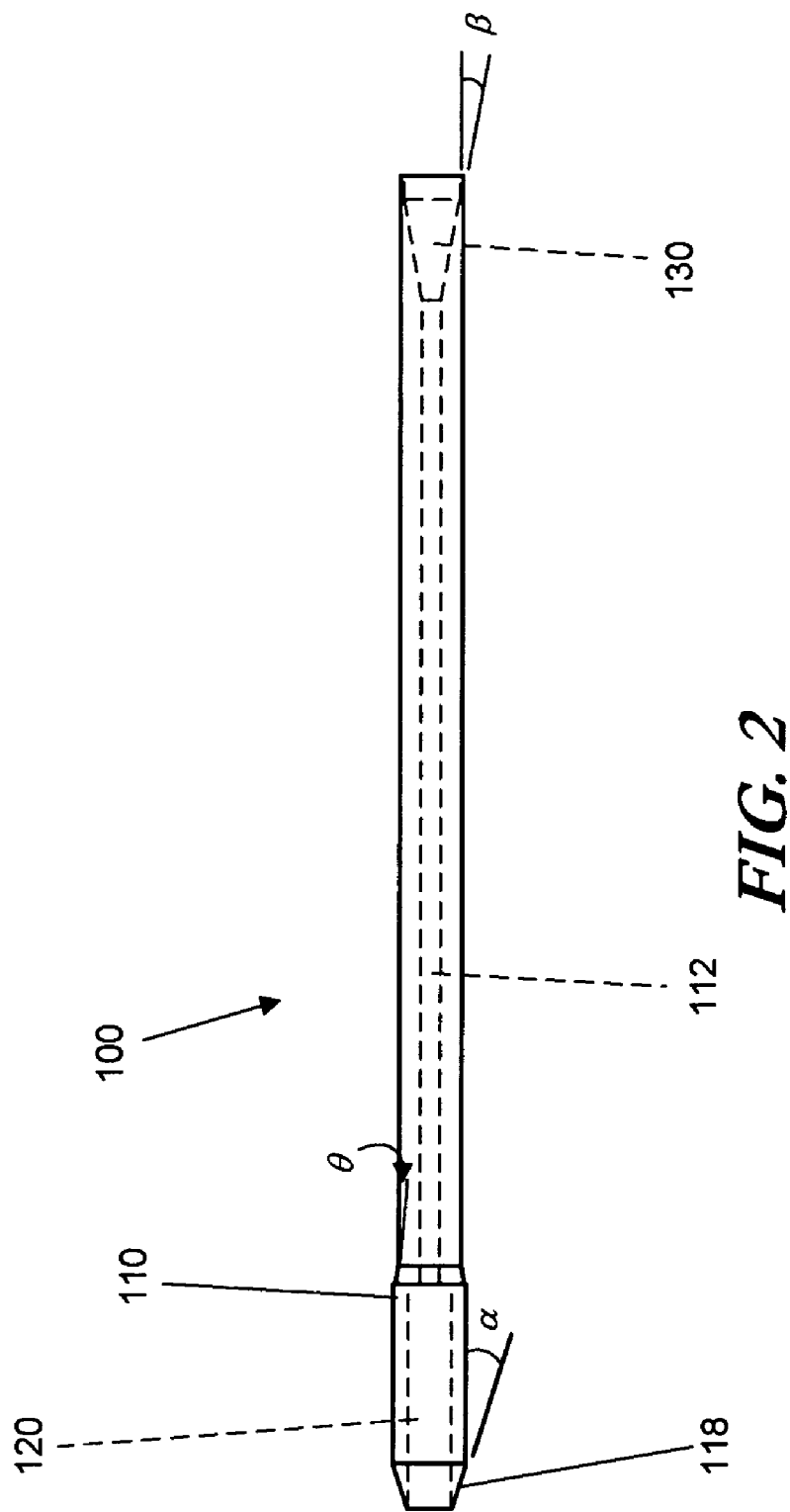
FIG. 2 is a side view of an embodiment of an after-loader in accordance with the present invention.
Figure 3:
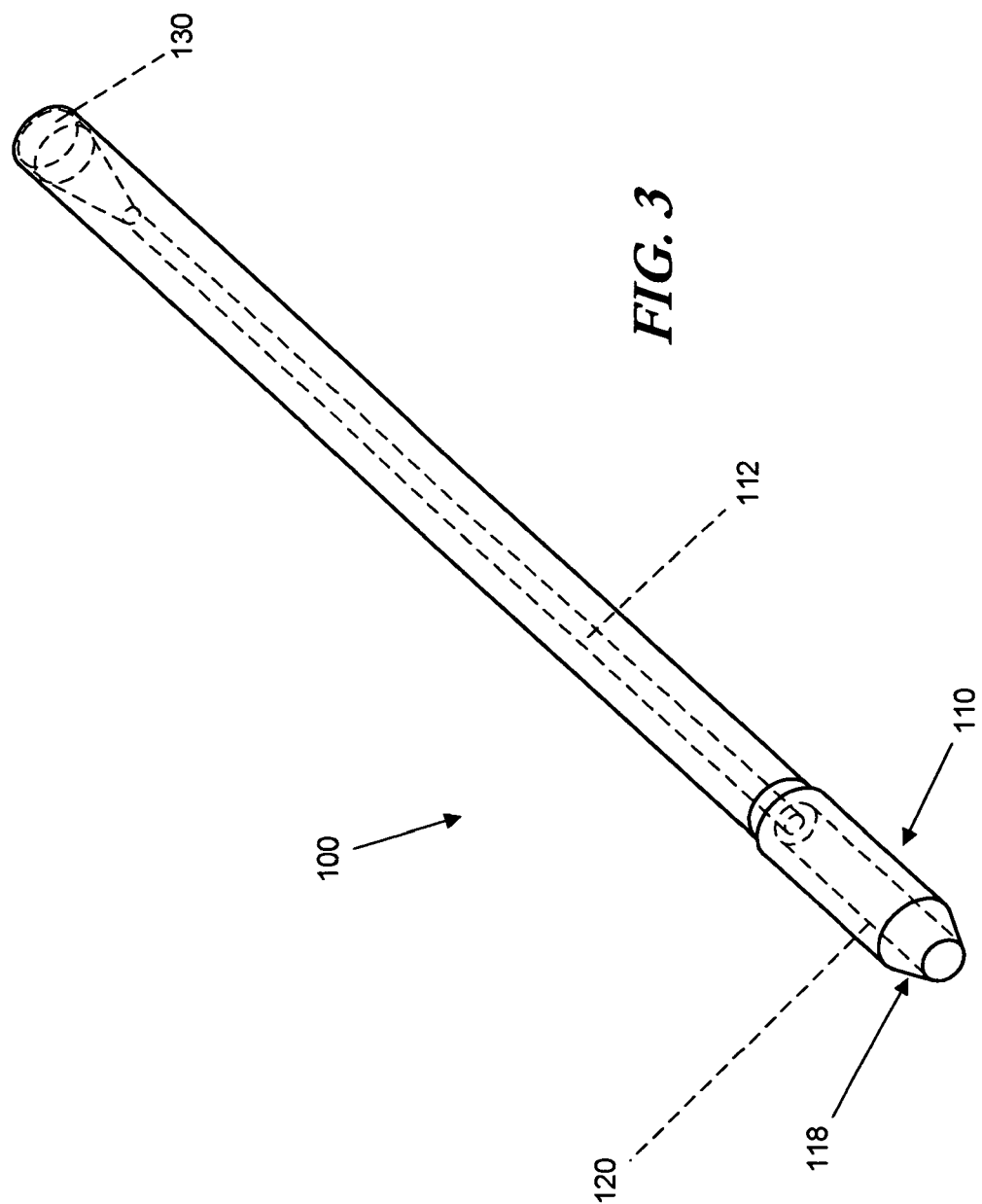
FIG. 3 is a perspective view of the after-loader of FIG. 2.

A hollow needle for use in Brachytherapy can include a MICK® needle or alternatively some other hollow needle, such as a seed lock needle. It has become a relatively common practice for physicians to employ needles other than MICK® needles; however, MICK® needles continue to be in popular use. A MICK® needle includes a hub positioned at a proximal end, the hub being a generally simple cylinder in shape. Referring to FIG. 1, a seed lock needle 4 differs from a MICK® needle in that the hollow needle 2 is coupled to a hub 6 having an enlarged diameter with a funneled proximal end 8 that typically screws onto a syringe. The funneled proximal end 8 allows a more forgiving tolerance for inserting implants into the hollow needle 2. However, tools for expediting and/or simplifying the loading process of the implant within the hollow needle are typically compatible with only one of multiple types of needles.

Referring to FIGS. 2, 3 and 5 through 7B, embodiments of after-loaders 100 in accordance with the present invention can simplify and/or expedite loading of implants into a needle. The after-loader 100 can accommodate a MICK® needle 160 (shown in FIG. 7B) within a bore 120 of a distal end 110 of the after-loader 100, or alternatively a seed lock needle 4 (shown in FIG. 7A), providing flexibility in hollow needle choice. The distal end 110 can include an enlarged diameter tapering at an angle θ from its largest diameter toward the proximal end of the after-loader 100 at some small angle. In accordance with an embodiment, the maximum diameter of the after-loader 100 near the distal end 110 is 3/16" necking down at a 5 degree angle. The purpose of this taper is to accept a shield 150 (shown in FIG. 6) over the outside of the after-loader 100, and to further provide a friction fit to lock the shield over the after-loader 100, the friction fit being attributable to the increase in diameter toward the distal end 110. The shield 150 is positioned around the after-loader 100 to reduce or minify an amount of radiation that escapes from the after-loader 100 where the implants placed in the after-loader 100 are radioactive. The after-loader 100 itself can be formed using a transparent plastic, for example by molding, but is not limited thereto. Where the after-loader 100 is formed of a plastic, the after-loader 100 does not sufficiently restrict radiation from escaping the after-loader 100; therefore, shielding is employed to prevent leakage. The shield 150 can be formed of some material that sufficiently restricts the amount of radiation that escapes the shield 150, such as stainless steel. In other embodiments, after-loaders 100 of the present invention can be formed from a different material more opaque to radiation, such as stainless steel. In such embodiments a separate shield is not necessary.

Figure 7A:
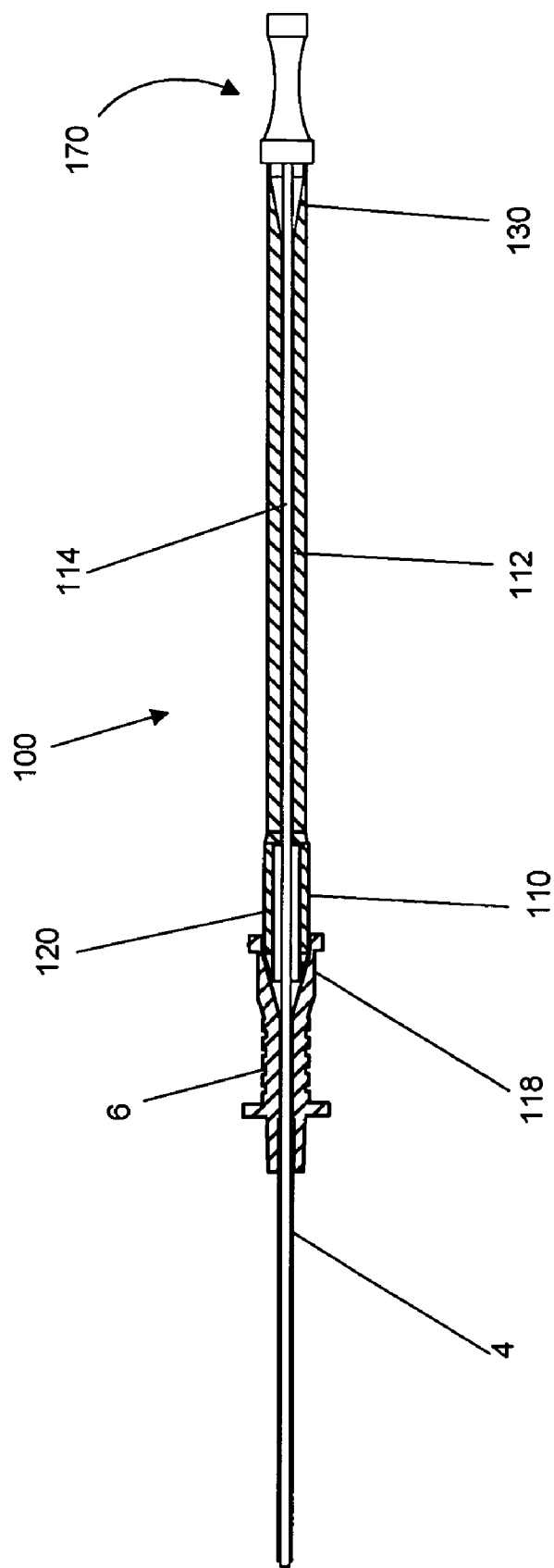
FIG. 7A is a cross-sectional side view of the after-loader of FIG. 1 mated with a needle, and having a stylet disposed within the after-loader and needle.
Figure 7B:
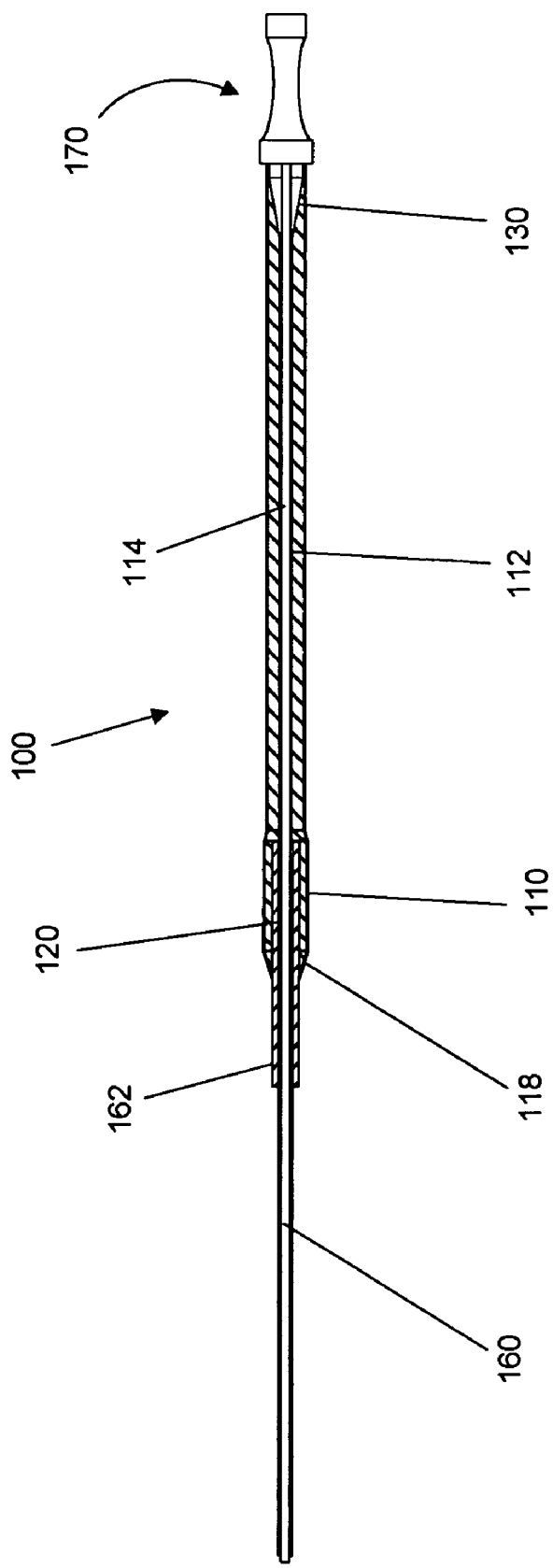
FIG. 7B is a cross-sectional side view of the after-loader of FIG. 2 mated with a needle, and having a stylet disposed within the after-loader and needle.

Referring to FIG. 7A, the nose 118 of the after-loader 100 is tapered at an angle α generally corresponding to an angle of the funneled proximal end 8 of a seed lock needle 4. Thus, an external angle of the nose end 118 can be approximately 15 degrees in angle, in an embodiment wherein a typical seed lock needle 4 is to be accommodated. The nose 118 of the after-loader 100 is positioned within the funneled proximal end 8 so that the after-loader 100 is removably mated with the hub 6 of the seed lock needle 4.

Figure 4D:
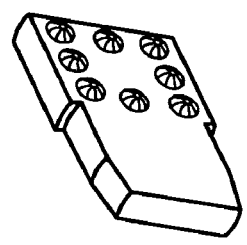
FIG. 4D is an alternative embodiment of a proximal end plug for use with the after-loader of FIG. 2.
Figure 4C:
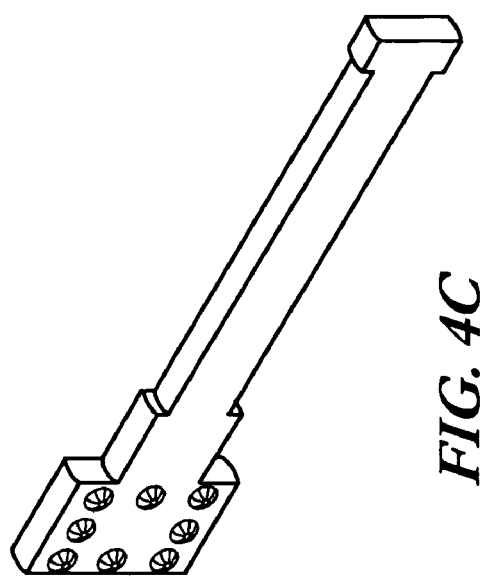
FIG. 4C is an alternative embodiment of a distal end plug for use with the after-loader of FIG. 2.
Figure 5:
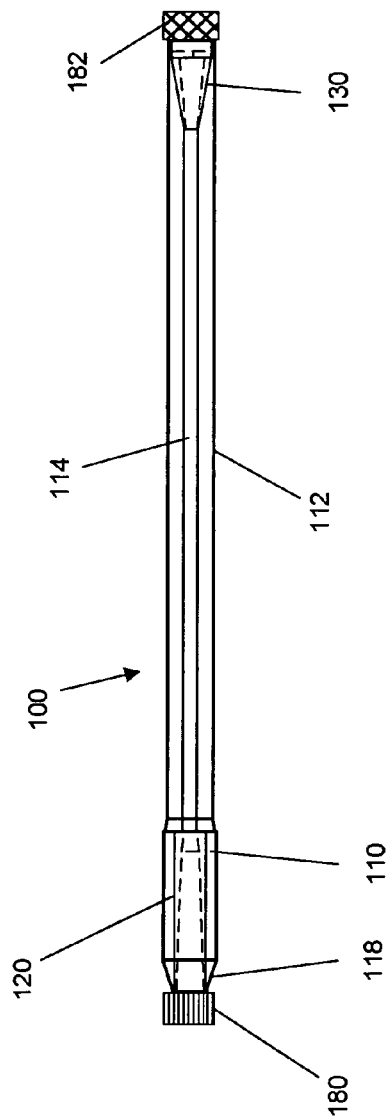
FIG. 5 is a side view of the after-loader of FIG. 2 with the distal end plug and proximal end plug in place.
Figure 6:
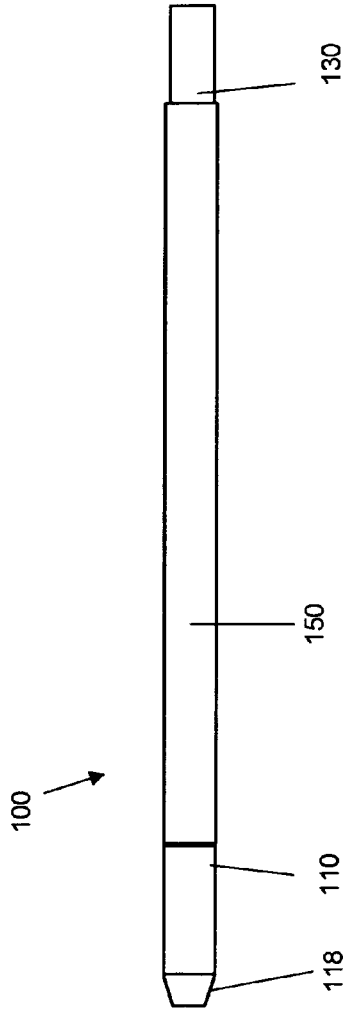
FIG. 6 is a side view of the after-loader of FIG. 2 with shielding arranged over a portion of the after-loader.

Still further, the distal end 110 of the after-loader 100 includes an enlarged diameter relative to the body 112 of the after-loader 100, which roughly corresponds to a diameter of a hollow needle. As further shown FIG. 7B, the distal end 110 is such that the enlarged diameter can accommodate the hub 162 of a MICK® needle 160, and in an embodiment the distal end 110 has a length generally sufficient to receive the hub 162 of the MICK® needle 160. Thus, the after-loader 100 can be removably mated with a MICK® needle or a seed lock needle, at the option of the physician. The funneled shape of the distal end 110 also accommodates a distal end plug 180 (shown in FIGS. 4A and 5) inserted into the distal end 110, the distal end plug 180 functioning to hold implants positioned within the after-loader 100 in place. The distal end plug 180 prevents implants from falling out of the after-loader 100, and further can be employed to block radiation from emitting from the end of the after-loader 100. It should be noted that the distal end plug 180 need not be shaped as shown in FIGS. 4A and 5. The distal end plug 180 need only be shaped so as to function to accommodate the implant within the after-loader 100. For example, where radiation emission from the longitudinal ends of implant is not a concern, the end plug need not function to block radiation. Thus, in some embodiments, for example, a distal end plug 280 as shown in FIG. 4C can be employed to resist undesired movement within the after-loader 100 and provide for removal, which as shown is accomplished by way of a textured surface 281.

An opening at the proximal end 130 of the after-loader 100 can be funneled having an angle β to simplify insertion into a bore 114 of the body 112 of the after-loader 100 an implant, or a stylet (also referred to herein as a push-rod). For example, the funnel can cause an increase in diameter at a 10 degree angle. The funneled shape of the opening at the proximal end 130 also accommodates a proximal end plug 182 (shown in FIGS. 4B and 5) inserted into the proximal end 130, the proximal end plug 182 functioning to hold implants positioned within the after-loader 100 in place. The proximal end plug 182 prevents implants from falling out of the after-loader 100, and further can be employed to block radiation from emitting from the end of the after-loader 100. The distal end plug 180 and proximal end plug 182 shown in FIGS. 4A-5 are merely embodiments of plugs for use with after-loaders in accordance with the present invention. In other embodiments, some other style of plug can be employed to retain an implant with an after-loader. In still other embodiments, plugs for use with the after-loader of the present invention can be integrally formed with an implant housed within the after-loader. The proximal end plug 182 need only be shaped so as to function to accommodate the implant within the after-loader 100. For example, where radiation emission from the longitudinal ends of the implant is not a concern, the end plug need not function to block radiation. Thus, in some embodiments, a distal end plug 282 as shown in FIG. 4D can be employed to resist undesired movement within the after-loader 100 and provide for removal, which as shown is accomplished by way of a textured surface 283.

Figure 8:
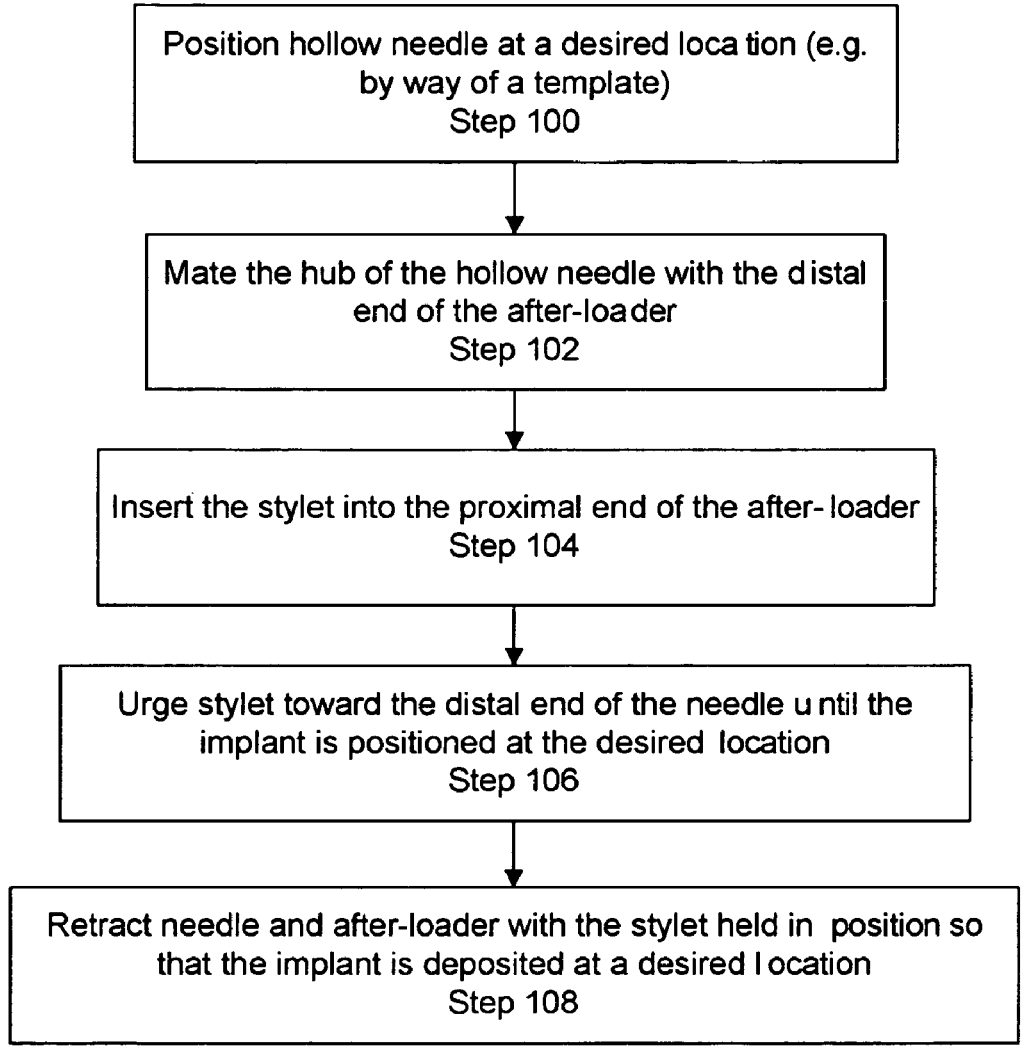
FIG. 8 is a flowchart of an embodiment of a method of using an after-loader in accordance with the present invention.
Figure 9:
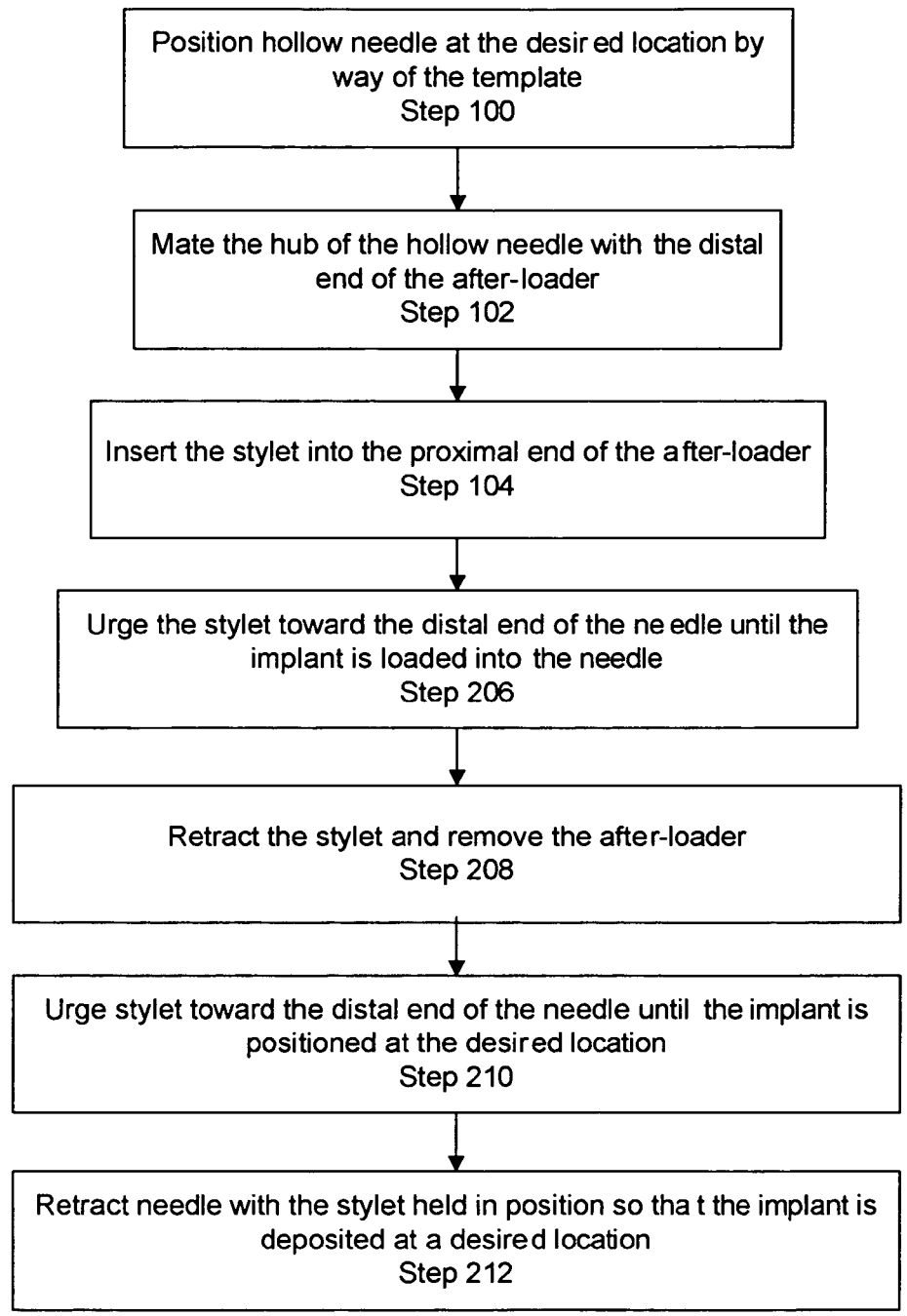
FIG. 9 is a flowchart of an alternative embodiment of a method of using an after-loader in accordance with the present invention.

Referring to FIG. 8, the distal end of a hollow needle is positioned at the desired location within a patient's body (e.g. by way of a template) prior to use of the after-loader 100 (Step 100). The hub of the hollow needle is mated with the distal end 110 of the after-loader 100 (Step 102), either by way of the tapered nose 118 or the bore 120 of the distal end 110. With the implant positioned within the after-loader 100 a stylet 170 (shown in FIGS. 7A and 7B) is inserted into the proximal end 130 of the after-loader 100 (Step 104) and is urged toward the distal end of the needle until the implant is positioned at the desired location (Step 106). The stylet 170 for use with the after-loader 100 can be sufficient in length to accommodate both the needle and the after-loader 100, which are retracted while the stylet 170 is held in position so that the implant is deposited at a desired location (Step 108). Referring to FIG. 9, alternatively, a stylet of less than sufficient length to accommodate both the needle and the after-loader 100 can be employed. When such a stylet is used, the stylet can urge the implant from the after-loader 100 to the hollow needle (Step 206). The stylet can then be removed, and the after-loader 100 disconnected (Step 208). The stylet 170 can then be reinserted into the hub of the needle to urge the implant to the desired location (Step 210). The needle can then be retracted with the stylet held in position so that the implant is deposited at a desired location (Step 212).

As mentioned, the after-loader 100 can be employed for use with a single seed, an anchor seed, multiple seeds with or without spacers between adjacent seeds, strands, a radioactive rod, or a radioactive coil, a marker, or some other implantable device. A strand can include a plurality of radioactive sources spaced apart from one another, e.g. in accordance with a treatment plan.

In further embodiments of after-loaders in accordance with the present invention, the after-loaders 100 can be pre-loaded with strands, loose seeds and spacers, or other implants so that the after-loader can be selected by the physician and used without loading by the physicians. Pre-configured strands, and other implants can be loaded into the after-loader 100 off-site and fitted with plugs at the proximal end 130 and the plugs to hold the ends in, and then shipped to the user and assigned to certain patients. Thus, the proper treatment can be determined as part of a pre-plan. In such embodiments, the after-loader would include shielding securely fitted to the outside surface of the after-loader 100. Such pre-loaded after-loaders can simplify and expedite the implantation process. Further, such pre-loaded after-loaders 100 offer benefits to hospitals or clinics that strive to minify the amount of handling of the implants performed by staff. It is also possible for a physician to load seeds, strands, or other implants into the after-loaders 100 before needles are inserted into a patient. As will be appreciated, and which can be extrapolated from the embodiments described, the after-loaders 100 can be longer or shorter in length as needed. For example, where an implant appropriate for a treatment plan is an anchor seed, the after-loaders 100 can have a length appropriate to the implant.

The after-loader 100 can include a diameter that, at a maximum, is at least 5 mm in size to generally match the pitch of a typical template. However, in other embodiments, the after-loader 100 can be larger or smaller in diameter.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. An after-loader for providing an implant to a hollow needle, the after-loader comprising:
a body having a distal end and a proximal end, the distal end including a bevel and a bore;
wherein the bevel is adapted to receive a hub of a first type of brachytherapy needle and the bore is adapted to receive a hub of a second type of brachytherapy needle; and
a radiation shield adapted to be provided over at least a portion of the body; and
wherein the distal end further includes a taper along a portion of a distance from the distal end to the proximal end for providing a friction fit to the shield.

2. The after-loader of claim 1, wherein:
the bore is a first bore; and
further comprising a second bore extending through the after-loader; and
wherein a portion of the second bore has an expanding funnel shape toward the proximal end.

3. The after-loader of claim 2, wherein the second bore is narrower than the first bore.

4. The after-loader of claim 2, wherein the second bore is adapted to receive a stylet.

5. The after-loader of claim 1, wherein:
the bevel is adapted to receive a hub of a seed lock needle.

6. A system for positioning implants within a body of a patient, the system comprising:
a needle having a hub;
an afterloader including a body, the body having:
a distal end including a bevel and a first bore;
a proximal end; and
a second bore extending approximately from the proximal end to the first bore;
wherein the bevel and the first bore are selectable for receiving a hub of a needle; and
a stylet receivable within the second bore; and
a radiation shield adapted to be provided over at least a portion of the body; and
wherein the distal end further includes a taper along a portion of a distance from the distal end to the proximal end for providing a friction fit to the shield.

7. The system of claim 6, wherein a portion of the second bore has an expanding funnel shape toward the proximal end.

8. The system of claim 6, wherein the second bore is narrower than the first bore.

9. The system of claim 6, wherein:
the bevel is adapted to receive a hub of a seed lock needle.

10. The system of claim 6, wherein:
the stylet has a distal end and a proximal end;
the proximal end of the stylet includes a hub adapted to be gripped; and
the distal end of the stylet has sufficient length to extend in a distal direction through the needle and afterloader.

11. An after-loader for providing an implant to a hollow needle, the after-loader comprising:
a body having a distal end and a proximal end and a bore extending therebetween;
at least one implant stored in the bore;
wherein the distal end is configured to be mated to a hub of a hollow needle;
wherein the proximal end is configured to accept a stylet; and
a radiation shield adapted to be provided over at least a portion of the body; and
wherein the distal end further includes a taper along a portion of a distance from the distal end to the proximal end for providing a friction fit to the shield.

12. The after-loader of claim 11, further comprising:
a pair of removable plugs to keep the at least one implant within the bore until the plugs are removed.

* * * * *